United States Patent [19]

Trott et al.

[11] Patent Number: 4,796,624
[45] Date of Patent: Jan. 10, 1989

[54] LASHLINER

[75] Inventors: Arthur F. Trott, Largo; Sam R. Marchand, Dunedin, both of Fla.

[73] Assignee: Concept, Inc., Clearwater, Fla.

[21] Appl. No.: 932,638

[22] Filed: Nov. 19, 1986

[51] Int. Cl.⁴ .......................... A61D 1/00; B43K 5/00
[52] U.S. Cl. ..................... 128/316; 81/9.22; 215/247; 604/86
[58] Field of Search .......... 81/9.22; 401/195; 215/247; 604/46, 86, 200, 245; 128/303 R; 126/316

[56] References Cited

U.S. PATENT DOCUMENTS

| 768,413 | 8/1904 | Wagner | 91/9.22 |
|---|---|---|---|
| 2,346,334 | 4/1944 | Shaw | 604/86 |
| 3,463,339 | 8/1969 | McGuckin | 215/247 |
| 3,502,097 | 3/1970 | Muller | 604/86 X |
| 3,509,786 | 5/1970 | Büttner | 81/9.22 |
| 3,637,102 | 1/1972 | Shaw | 215/247 |
| 3,688,764 | 9/1972 | Reed | 604/46 |
| 3,850,174 | 11/1974 | Ayres | 215/247 |
| 3,905,371 | 9/1975 | Stickl | 604/46 |
| 4,163,500 | 8/1979 | Gunne et al. | 215/247 X |
| 4,204,438 | 5/1980 | Bingris | 81/9.22 |
| 4,299,506 | 11/1981 | Hashimoto | 401/195 |
| 4,582,060 | 4/1986 | Bailey | 128/316 |
| 4,664,952 | 2/1987 | Patipa | 128/305 |
| 4,665,912 | 5/1987 | Burton | 128/303 R |
| 4,719,825 | 1/1988 | Le Haye et al. | 128/316 X |

FOREIGN PATENT DOCUMENTS 1587519  4/1981  United Kingdom ................. 81/9.22

Primary Examiner—Richard J. Apley
Assistant Examiner—Robert W. Bahr
Attorney, Agent, or Firm—Frijouf, Rust & Pyle

[57] ABSTRACT

An apparatus is disclosed for introducing a liquid within a material. The apparatus comprises a body member having an internal cavity for receiving a battery. An end member is secured to the body member for supporting a needle guide extending through the end member for slidably receiving a needle. A reciprocal coupling means interconnects the motor and the needle for reciprocating the needle relative to the end member upon rotation of the motor. A reservoir is in fluid communication with the needle for retaining the liquid therein and for enabling the liquid to flow along the needle. The reciprocating needle creates a plurality of perforations in the material enabling the liquid to flow along the needle to enter the perforations. The apparatus is suitable for introducing a liquid pigment into a skin tissue such as introducing a permanent eyeliner into an eyelid.

18 Claims, 3 Drawing Sheets

4,796,624

LASHLINER

BACKGROUND OF THE INVENTION

1. Field of the Invention

This invention relates to fluid introduction and more particularly to the perforation of a material and the introduction of a liquid within the perforation.

2. Information Disclosure Statement

Various types of apparati have been devised in the past for the introduction of a liquid within a material. A specific type of this introduction includes the perforation of the material and the introduction of the liquid through the perforation in the material. For example, numerous apparati are available in the prior art for perforating material such as living tissue for introducing a liquid such as a liquid pigment into a perforation. The ancient art of tattooing involves the perforation of skin tissue with a needle and the introduction of a pigmented liquid into the perforation to provide a permanent indicia or design under the skin tissue. The tattooing art subsequently progressed with the introduction of electric needles for quickly perforating the tissue to allow for the introduction of the liquid pigment therein.

More recently, license physicians have been requested to introduce a liquid pigment into the eyelid of a person to provide a permanent eyeliner. The permanent eyeliner has a distinct advantage of eliminating the need for using pencil-type pigments and the like. Furthermore, the permanent eyeliner will not wash off even when immersed in water. Permanent eyeliners find many advantages in an age of active people. Furthermore, permanent eyeliner is desirable for persons wearing contact lenses since the possibility of the eyeliner falling into the eye is essentially eliminated.

Accordingly, it is an object of the present invention to provide an apparatus for introducing a liquid within a material wherein the apparatus has a reciprocating needle means for perforating a material and a liquid reservoir introducing the liquid material into the perforation.

Another object of this invention is to provide an apparatus for introducing a liquid within a material which is self-contained having a power supply disposed internally therein.

Another object of this invention is to provide an apparatus for introducing a liquid within a material which is designed and constructed to standards commensurate with other medical devices.

Another object of this invention is to provide an apparatus for introducing a liquid within a material which is lightweight and low cost making the apparatus suitable for disposable use.

Another object of this invention is to provide an apparatus for introducing a liquid within a material which may be adapted for introducing a liquid pigment into tissue.

Another object of this invention is to provide an apparatus for introducing a liquid within a material wherein the apparatus meters a selected quantity of liquid flow into perforations created by a reciprocating needle.

Another object of this invention is to provide an apparatus for introducing a liquid within a material which may be readily sterilized and transported in a sterile container.

The foregoing has outlined some of the more pertinent objects of the present invention. These objects should be construed to be merely illustrative of some of the more pertinent features and applications of the invention. Many other beneficial results can be obtained by applying the disclosed invention is a different manner or modifying the invention within the scope of the disclosure. Accordingly, other objects and a fuller understanding of the invention man be had by referring to the summary of the invention and the detailed description describing the preferred embodiment in addition to the scope of the invention defined by the claims taken in conjunction with the accompanying drawings.

SUMMARY OF THE INVENTION

The invention is defined by the appended claims with a specific embodiment shown in the attached drawings. For the purpose of summarizing the invention, the invention may be incorporated into an apparatus and method for introducing a liquid within a material comprising a body member having an interior cavity for receiving motor means therein. An end member is secured to the body member with the end member having a needle guide extending therethrough for slidably mounting a needle means. A reciprocal coupling means interconnects the motor means and the needle means for reciprocating the needle means relative to the end member upon rotation of the motor means. The reciprocal needle means creates a plurality of perforations in the material. A reservoir in fluid communication with the needle means retains the liquid and enables the liquid to flow along the needle means to enter the plurality of perforations in the material.

In a more specific embodiment of the invention, the body member is substantially a cylindrical body member having a cylindrical internal cavity which is dimensioned for receiving battery means therein for supplying electrical power to the motor means. The end member is secured to the body member with the needle guide comprising a tubular member for slidably receiving the needle means therein. The reservoir preferably comprises an internal cavity disposed in the end member with a filling aperture communicating with the internal cavity for filling the internal cavity with the liquid. A perforatable reservoir membrane permits the use of a needle and syringe for delivering liquid to the reservoir by piercing the perforatable membrane to access the filling aperture. The perforatable reservoir membrane self-seals upon withdrawing the liquid delivering needle therefrom and also seals the filling aperture to retain the liquid within the internal cavity. Preferably, the perforatable membrane is permanently affixed to the end member to enhance the sealing of the filling aperture.

In one embodiment, the reciprocal coupling means includes a cylindrical cam secured to one of the motor means and the needle means and a cam follower secured to the other of the motor means and the needle means for reciprocating the needle means relative to the end member upon rotation of the motor means. A seal cooperates with the reciprocal coupling means for sealing the reservoir from the interior cavity of the body member.

The apparatus preferably includes a switch electrically interposed between the motor means and the battery means for controlling the rotation of the motor. A needle cover may be removably secured to the body member for covering the needle means. The needle cover cooperates with the switch for permitting operation of the switch to enable rotation of the motor means when the needle cover is removed from the body member. The needle cover further cooperates with the switch for inhibiting the operation of the switch to prevent rotation of the motor when the needle cover is secured to the body member.

In a more specific embodiment of the invention, the apparatus may be adapted for introducing a liquid pigment into a tissue. In this embodiment, the apparatus may be instructed to be a low-cost, disposable apparatus for use with a single pigmented liquid. The apparatus may be also specifically designed to be easily sterilized and to be transported in a sterile container.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE DRAWINGS

Figure 1:
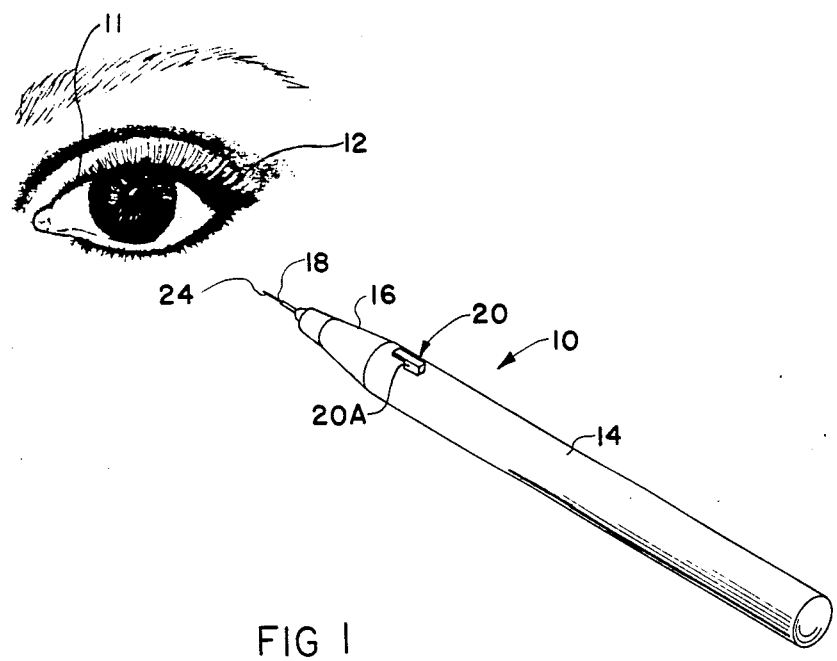
FIG. 1 is an isometric view of the apparatus of the present invention applying a permanent eyeliner to an eyelid.

FIG. 1 is an isometric view of an apparatus 10 in the operative position for introducing a liquid within a material. In this embodiment, the apparatus 10 is adapted for introducing a liquid such as pigmented liquid 11 into an eyelid 12 but it should be understood that the apparatus 10 may have various applications in the art. The apparatus 10 comprises a body member 14, an end member 16 and needle means 18. An internal switch 20 has a switch button 20A which extends outwardly from the body member 14 to activate the apparatus 10 and thereby reciprocate the needle means 18 relative to the body member 14. As it will be hereinafter described, the reciprocating needle means 18 introduces the liquid 11 material such as a pigmented liquid 11 into the eyelid tissue to provide a permanent eyeliner for the eyelid 12.

Figure 2:
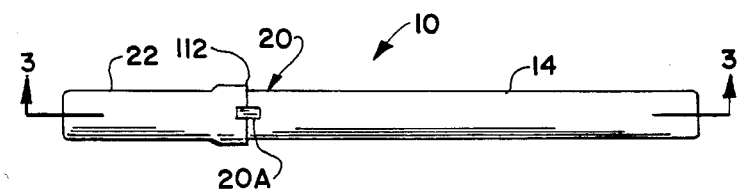
FIG. 2 is a top elevational view of the apparatus of FIG. 1 with a needle cover secured thereto.

FIG. 2 illustrates a top view of the apparatus 10 with a needle cover 22 frictionally engaging the body member 14 to protect a distal end 24 of the needle means 18 when the apparatus 10 is not in use.

Figure 3:
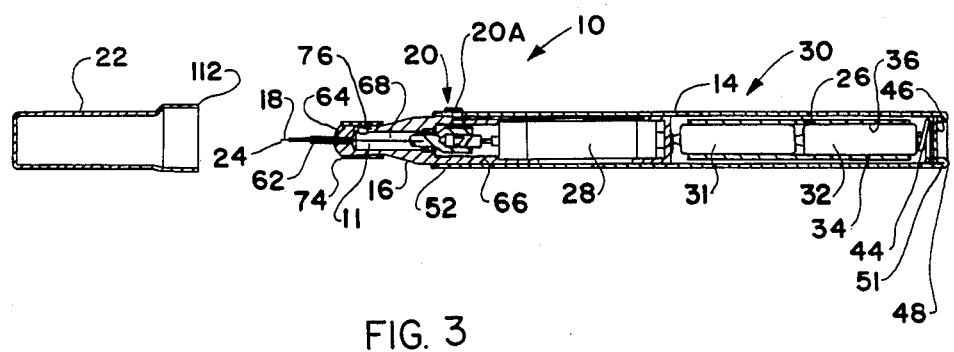
FIG. 3 is a sectional view along line 3—3 in FIG. 2 with the needle cover being removed.

FIG. 3 is a sectional view along line 3—3 in FIG. 2 with the needle cover 22 being removed which illustrates in greater detail the internal mechanism of the apparatus 10. The body member 14 includes an interior cavity 26 for receiving a motor 28 and battery means 30 shown as a first and second battery 31 and 32. The body member 14 is preferably made of a moldable plastic material or other suitable insulating material and the like. A cylindrical battery sleeve 34 receives the first and second batteries 31 and 32 therein with an interior surface 36 of the cylindrical battery sleeve 34 frictionally engaging the outer surfaces of the first and second batteries 31 and 32. The cylindrical battery sleeve 34 enables the first and second batteries 31 and 32 to be inserted into the interior cavity 26 of the body member 14 as a single unit.

Figure 4:
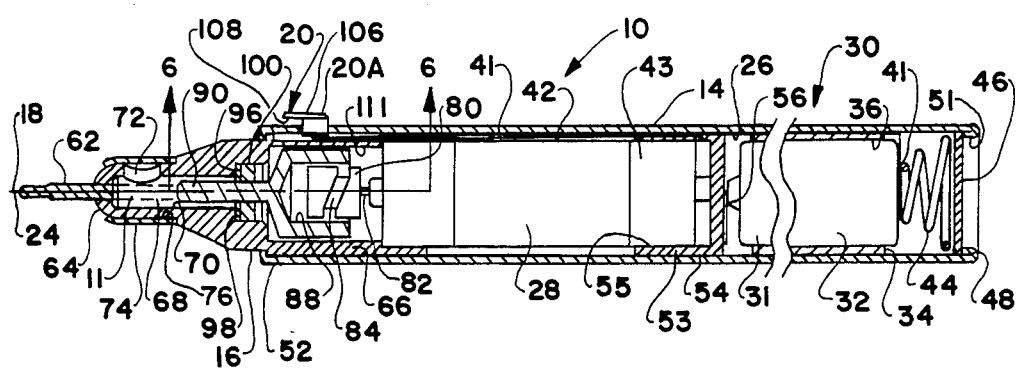
FIG. 4 is an enlarged view of FIG. 3.
Figure 5:
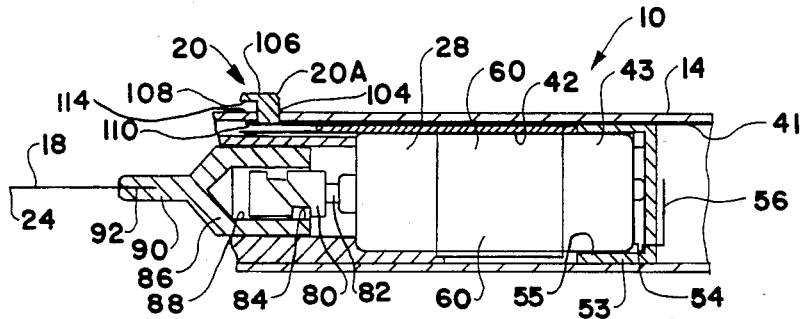
FIG. 5 is an enlarged view of a subassembly of the apparatus of FIG. 3.

FIGS. 4 and 5 illustrate in greater detail a first conductor 41 shown as a flattened resilient metallic conductor extending from a negative terminal of the second battery 32 along the interior cavity 26 of the body member 14 to the switch 20. A second conductor 42 extends from a metallic outer surface 43 of the motor 28 to the switch 20l. The operation of the switch 20 and the switch button 20A and the first and second conductors 41 and 42 will be explained in greater detail hereinafter.

A biasing spring 44 engages an end plate 46 to provide a bias to the first and second batteries 31 and 32 ina direction to the left in FIG. 4. The body member 14 is shown having a stop 48 located at a first end 51 of the body member 14 whereas the end member 16 is disposed at a second end 52 of the body member 14. The stop 48 engages the end plate 46 for forming a support for the biasing spring 44. In this embodiment, the stop 48 is fabricated by rolling the first end 51 of the body member 14. The biasing spring 44 also enables the end plate 46 to be moved towards the left in FIG. 4 to provide a space required for a machine to deform the first end 51 of the body member 14 into the stop 48. Thereafter, the bias spring 44 returns the end plate 46 to the position shown in FIGS. 3 and 4.

An insulating sleeve 53 has an outer surface 54 which frictionally engages the interior cavity 26 of the body member 14. The insulating sleeve 53 also includes an interior sleeve opening 55 for frictionally receiving a portion of the metallic outer surface 43 of the motor 28. The insulating sleeve 53 positions the motor 28 within the interior cavity 26 of the body member 14. An electrical connector 56 extends from one pole of the motor 28 to contact a positive terminal of the first battery 31. The second conductor 42 engages the metallic outer surface 43 of the motor 28 which is connected to the other pole of the motor 28. The second conductor 42 extends within the interior sleeve opening 55 of the motor sleeve 53 to insure proper electrical contact with the metallic outer surface 43 of the motor 28 and to maintain proper position of the second conductor 42.

Figure 8:
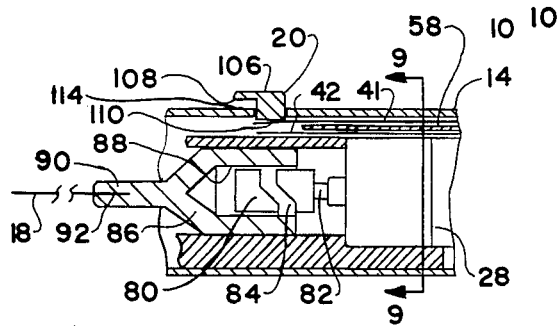
FIG. 8 is an enlarged sectional view of a portion of FIG. 2.
Figure 9:
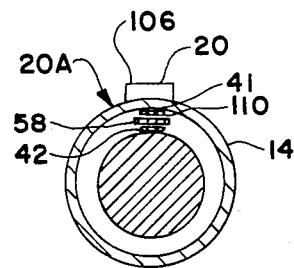
FIG. 9 is a sectional view along line 9—9 of FIG. 8.

As also shown in FIGS. 8 and 9, an insulator 58 is disposed between the first and second conductors 41 and 42 and is maintained in position by an insulating sleeve 60. Accordingly, upon the depression of the switch button 20A, the first conductor 41 contacts the second conductor 42 to complete an electrical circuit between the motor 28 and the first and second batteries 31 and 32.

The end member 16 is preferably made of a unitary plastic material which is received within the second end 52 of the body member 14. The end member 16 comprises a needle guide 62 shown as a tubular metallic member secured to an outer end 64 of the end member 16. An inner end 66 of the end member 16 is secured to the second end 52 of the body member 14 by suitable means such as adhesives, sonic welding or the like. The needle guide 62 slidably mounts the needle means 18 therein and provides a guide for the reciprocating needle means 18. The needle guide 62 also provides a channel for the liquid 11 to flow from a reservoir 68 to the distal end 24 of the needle means 18. In this embodiment, the reservoir 68 is shown as an internal cavity 70 defined in the end member 16 and being in fluid communication with the needle guide 62. The reservoir 68 includes a filling aperture 72 for filling the reservoir 68 with the liquid 11. A perforatable reservoir membrane 74 covers and seals the filling aperture 72. In this embodiment, the preforatable reservoir membrane 74 is shown as a resilient member which permanently engages an outer cylindrical surface 76 of the end member 16 to seal the filling aperture 72. The perforatable reservoir membrane 74 self-seals to permit the use of a needle and syringe to deliver liquid to the reservoir 68 by piercing the perforatable reservoir membrane 74 with a liquid delivering needle to access the filling aperture 72. The self-sealing perforatable reservoir membrane 74 maintains the liquid internal the filling aperture 72 and reservoir 68 upon withdrawal of the liquid delivering needle therefrom.

Figure 6:
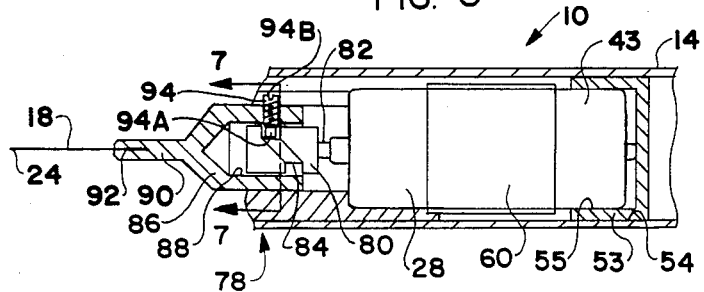
FIG. 6 is a partial sectional view along line 6—6 in FIG. 4.
Figure 7:
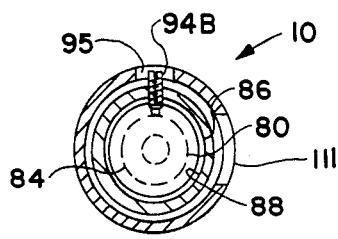
FIG. 7 is a sectional view along line 7—7 in FIG. 6.

A reciprocal coupling means 78 also shown in FIGS. 5-7 comprises a cylindrical cam 80 secured to a shaft 82 of the motor 28 for rotating the cylindrical cam 80 with the rotation of the motor shaft 82. A cam groove 84 is formed within the cylindrical cam 80. The reciprocal coupling means 78 also includes a cam follower 86 having an internal cylindrical region 88 for receiving the cylindrical cam 80 therein. Cam follower 86 also includes a cam follower base 90 for mounting a proximal end 92 of the needle means 18. A cam follower tooth 94 shown as a threaded fastener has a first end 94A for engaging the cam groove 84 to reciprocate the cam follower 86 and the needle means 18 upon rotation of the motor 28. A second end 94B of the cam follower tooth 94 extends outwardly from the cam follower 86 to be slidably received within a slot 95 defined within the end member 16. The sliding cooperation between the cam follower tooth 94 and the slot 95 prevents the cam follower 86 from rotating within the end member 16.

A seal 96 is disposed within an undercut shoulder 98 within the end member 16. A seal retainer 100 secures the seal 96 into engagement with the undercut shoulder 98. The seal 96 insures that the liquid 11 within the reservoir 68 does not enter the interior cavity 26 of the body member 14.

Figure 10:
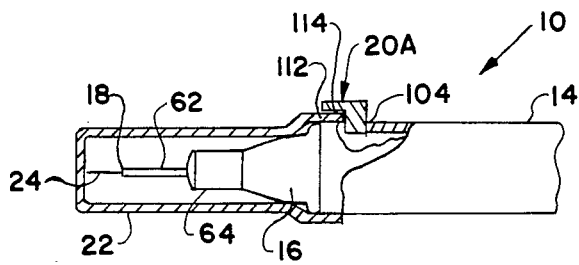
FIG. 10 is an enlarged side sectional view similar to FIG. 8 with the needle cover being in place.

The body member 14 includes a switch aperture 104 for receiving the switch button 20A therethrough. The switch button 20A as shown in FIGS. 8-10 includes an enlarged outer region 106 having an overhang 108. An interior region 110 of the switch button 20A engages the resilient first conductor 41 within the interior cavity 26 of the body member 14. The first conductor 42 is spaced apart from the second conductor 42 within a slot 111 defined in the end member 16. Upon depression of the enlarged outer region 106 of the switch button 20A, the interior region 110 bends the resilient first conductor 41 into electrical contact with the second conductor 42 to provide electrical power to the motor 28 for reciprocating the needle means 18. Upon releasing the enlarged outer region 106 of the switch button 20A, the resiliency of the first electrical conductor 41 returns the switch button 20A to the unattended and off position as shown in FIGS. 8 and 9. Accordingly, the apparatus 10 is entirely self-contained with internal batteries making the apparatus suitable for low cost production and capable of being used as a disposable unit.

When the needle cover 22 is frictionally secured to the body member 14, an end 112 of the needle cover 22 underlies the overhang 108 of the switch button 20A as shown in FIG. 10. Since the end 112 is disposed between the overhang 108 and an outer surface 114 of the body member 14, the end 112 prevents depression of the switch button 20A when the needle cover 22 is disposed upon the body member 14. Removal of the needle cover 22 allows the apparatus 10 to operate as intended.

The apparatus 10 may be readily assembled in the following manner. The needle guide 62 is first secured to the outer end 64 of the end member 16. The inner end 66 of the end member 16 is secured to the second end 52 of the body member 14. The switch button 20A is then inserted through the switch aperture 104 of the body member 14. Thereafter, the subassembly shown in FIG. 5 comprising the motor 28, the reciprocating coupling means 78, the needle 18 means and the first and second conductors 41 and 42 is introduced into the interior cavity 26 of the body member 14 through the first end 51 of the body member 14. The cylindrical battery sleeve 34 containing the first and second batteries 31 and 32 is then placed through the first end 51 of the body member 14 such that a positive terminal of the first battery 31 engages the electrical connector 56. The end of the first conductor 41 is bent into contact with the negative terminal of the second battery 32. Spring 44 and end plate 46 are then placed adjacent a negative terminal of the second battery 32 and the first end 51 of the body member 14 is rolled to form the stop 48. Thereafter, the needle cover 22 is placed onto the body member 14 to protect the distal end 24 of the needle means 18 and to inhibit depression of the switch button 20A. The ease of assembly of the apparatus 10 enables the device to be sterilized prior to shipment in a sterile container.

During the operation of the apparatus 10, the needle cover 22 is first removed and the reservoir cover 74 is displaced for introducing the liquid 11 into the reservoir 68. The reservoir cover 74 is then replaced to seal the filling aperture 72. Thereafter, an operator can simultaneously perforate and introduce the liquid 11 into the material such as tissue and the like. The reciprocal movement of the needle means 18 within the reservoir 72 enables the liquid 11 to flow between the needle means 18 and the needle guide 62 to meter the proper amount of liquid 11 to the distal end 24 of the needle means 18. The liquid 11 enters the perforations in the material or tissue to provide a permanent pigmentation or the like within the material. Upon the completion of the task, the apparatus 10 may be discarded thus eliminating the need for cleaning the reservoir 68 of the pigmented liquid 11 and resterilizing the apparatus 10.

Figure 11:
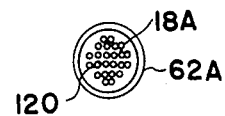
FIG. 11 is an enlarged end view of a second embodiment of a needle means.

FIG. 11 illustrates an end view of a variation of the needle means 18A. In this embodiment, the needle means 18A comprises a plurality of needles arranged in a generally cylindrical array 120. The cylindrical array 120 is disposed within a needle guide 62A. The cylindrical array 120 enables an operator to introduce a wider line of pigmented liquid 11 in a single stroke relative to a single needle means. It should be appreciated that the needle means may comprise a single or a plurality of needles with the plurality of needles established in various arrays.

The foregoing apparatus provides a low cost, economical and disposable means for introducing a liquid within the material. Although the apparatus has been disclosed with specific reference to the introduction of a liquid into the tissue, it should be understood that apparatus may find application with various material which may be perforated by the distal end of the needle means.

The present disclosure includes that contained in the appended claims as well a that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed:

1. An apparatus for introducing a liquid within a material, comprising:
    a body member having an interior cavity;
    motor means disposed in said interior cavity of said body member;
    an end member secured to said body member;
    needle means;
    needle guide extending through said end member for slidably mounting said needle means;
    reciprocal coupling means interconnecting said motor means and said needle means for reciprocating said needle means relative to said end member upon rotation of said motor means;
    said reciprocating needle means being capable of creating a plurality of perforations in the material;
    reservoir means in fluid communication with said needle means for retaining the liquid therein and for enabling the liquid to flow along said needle means to enter the plurality of perforations in the material upon reciprocation of said needle means;
    said reservoir further including an internal cavity disposed in said end member;
    said end member further including a filling aperture communicating with said internal cavity for filling said internal cavity with the liquid; and
    a perforatable reservoir membrane for covering said filling aperture to retain the liquid in said internal cavity and for permitting in use piercing by a liquid delivering needle to deliver the liquid to said reservoir and to self-seal upon withdrawal of said liquid delivering needle from said perforatable reservoir membrane.

2. An apparatus for introducing a liquid within a material as set forth in claim 1, wherein said body member is a cylindrical body member having a cylindrical interior cavity; and
    said cylindrical interior cavity being dimensioned for receiving battery means therein for supplying electrical power to said motor means.

3. An apparatus for introducing a liquid within a material as set forth in claim 2, wherein said end member is secured to an end of said cylindrical body member;
    said needle guide comprising a tubular member extending through said end member for slidably receiving said needle means therein.

4. An apparatus for introducing a liquid within a material as set forth in claim 1, wherein said perforatable reservoir membrane comprises a resilient member encircling said end member wherein said resilient member is permanently affixed to said end member.

5. An apparatus for introducing a liquid within a material as set forth in claim 1, wherein said reciprocal coupling means comprises a cylindrical cam secured to one of said motor means and said needle means; and
    a cam follower secured to the other of said motor means and said needle means for reciprocating said needle means relative to said end member upon rotation of said motor means.

6. An apparatus for introducing a liquid within a material as set forth in claim 5, including a seal cooperating with said reciprocal coupling means for sealing said reservoir means from said interior cavity of said body member.

7. An aparatus for introducing a liquid within a material as set forth in claim 1, wherein said reciprocal coupling means comprises a cylindrical cam secured to said motor means cooperating with a cam follower secured to said needle means for reciprocating said needle means relative to said end member upon rotation of said motor means.

8. An apparatus for introducing a liquid with a material as set forth in claim 1, including a switch electrically interposed between said motor means and the battery means for controlling the rotation of said motor means.

9. An apparatus for introducing a liquid within a material as set forth in claim 8, including a needle cover removably secured to said body member for covering said needle means; and
    said needle cover permitting operation of said switch to enable rotation of said motor means when said needle cover is removed from said body member and inhibiting operation of said switch to prevent rotation of said motor means when said needle cover is secured to said body member.

10. An apparatus for introducing a liquid within a material as set forth in claim 1, wherein said needle means comprises a plurality of needles established in a generally cylindrical array.

11. An apparatus for introducing a liquid pigment into tissue, comprising:
    a body member having an interior cavity;
    motor means disposed in said interior cavity of said body member;
    said interior cavity being dimensioned for receiving battery means therein for supplying electrical power to said motor means;
    an end member secured to an end of said body member;
    needle means;
    a tubular member extending through said end member for slidably receiving said needle means therein;

reciprocal coupling means comprising a cam and cam follower interconnecting said motor means and said needle means for reciprocating said needle means relative to said end member upon rotation of said motor means;

said reciprocating needle means being capable of creating a plurality of perforations in the tissue;

reservoir means comprising an internal cavity disposed in said end member and in fluid communication with said needle means for retaining the liquid pigment therein and for enabling the liquid pigment to flow along said needle means to enter the plurality of perforations in the tissue upon reciprocation of said needle means;

a filling aperture communicating with said internal cavity of said end member for filling said internal cavity with the liquid pigment; and a perforatable reservoir membrane for covering said filling aperture to retain the liquid in said internal cavity and for permitting in use piercing by a liquid delivering needle to deliver the liquid to said reservoir and to self-seal upon withdrawal of said liquid delivering needle from said perforatable reservoir membrane; and a switch electrically interposed between said motor means and the battery means for controlling the rotation of said motor means.

12. An apparatus for introducing a liquid pigment within a tissue as set forth in claim 11, wherein said perforatable reservoir membrane comprises a resilient member encircling said end member wherein said resilient member is permanently affixed to said end member.

13. An apparatus for introducing a liquid pigment within a tissue as set forth in claim 11, wherein said reicprocal coupling means comprises said cam being secured to said motor means; and said cam follower being secured to said needle means for reciprocating said needle means relative to said end member upon rotation of said motor means.

14. An apparatus for introducing a liquid pigment within a tissue as set forth in claim 11, including a needle cover removably secured to said body member for covering said needle means; and said needle cover permitting operation of said switch to enable rotation of said motor means when said needle cover is removed from said body member and inhibiting operation of said switch to prevent rotation of said motor means when said needle cover is secured to said body member.

15. An apparatus for introducing a liquid pigment into tissue, comprising:

a cylindrical body member having a cylindrical interior cavity;

motor means disposed in said cylindrical interior cavity of said cylindrical body member;

said cylindrical interior cavity being dimensioned for receiving battery means therein for supplying electrical power to said motor means;

an end member secured to an end of said cylindrical body member;

a plurality of needles established in a substantially cylindrical array;

a tubular member extending through said end member for slidably receiving said plurality of needles therein;

reciprocal coupling means comprising a cam and a cam follower interconnecting said motor means and said plurality of needles for reciprocating said plurality of needles relative to said end member upon rotation of said motor means;

said reciprocating plurality of needles being capable of creating a plurality of perforations in the tissue;

reservoir means comprising an internal cavity disposed in said end member and in fluid communication with said plurality of needles for retaining the liquid pigment therein;

a filling aperture communicating with said internal cavity of said end member for filling said internal cavity with the liquid pigment;

a perforatable reservoir membrane for covering said filling aperture to retain the liquid in said internal cavity and for permitting in use piercing by a liquid delivering needle to deliver the liquid to said reservoir and to self-seal upon withdrawal of said liquid delivering needle from said perforatable reservoir membrane;

said reservoir means enabling the liquid pigment to flow along said plurality of needles to enter the plurality of perforations in the tissue upon reciprocation of said plurality of needles;

a switch electrically interposed between said motor means and the battery means for controlling the rotation of said motor means;

a needle cover removably secured to said body member for covering said plurality of needles; and said needle cover permitting operation of said switch to enable rotation of said motor means when said needle cover is removed from said body member and inhibiting operation of said switch to prevent rotation of said motor means when said needle cover is secured to said body member.

16. An apparatus for introducing a liquid pigment within a tissue as set forth in claim 15, wherein said perforatable reservoir membrane comprises a resilient member encircling said end member wherein said resilient member is permanently affixed to said end member.

17. An apparatus for introducing a liquid pigment within a tissue as set forth in claim 15, wherein said reciprocal coupling means comprises said cam being secured to said motor means; and said cam follower being secured to said plurality of needles for reciprocating said plurality of needles relative to said end member upon rotation of said motor means.

18. An apparatus for introducing a liquid pigment into tissue, comprising:

a body member having an interior cavity;

motor means disposed in said interior cavity of said body member;

said interior cavity being dimensioned for receiving battery means therein for supplying electrical power to said motor means;

an end member secured to an end of said body member;

needle means;

a tubular member extending through said end member for slidably receiving said needle means therein;

reciprocal coupling means comprising a solid cylindrical cam having a groove formed therein;

a cam follower interconnecting said motor means and said needle means for reciprocating said needle means relative to said end member upon rotation of said motor means;

a cam follower tooth with a first end for engaging said cam groove to reciprocate said cam follower and said needle means upon rotation of said motor;

said cam follower tooth having a second end extending outwardly from said cam follower to be slidably received within a slot defined within said end member such that in use said cam follower is prevented from from rotating within said end member;

said reciprocating needle means being capable of creating a plurality of perforations in the tissue;

reservoir means comprising an internal cavity disposed in said end member and in fluid communication with said needle means for retaining the liquid pigment therein and for enabling the liquid pigment to flow along said needle means to enter the plurality of perforations in the tissue upon reciprocation of said needle means; and a switch electrically interposed between said motor means and the battery means for controlling the rotation of said motor means.

* * * * *